Figure 1:
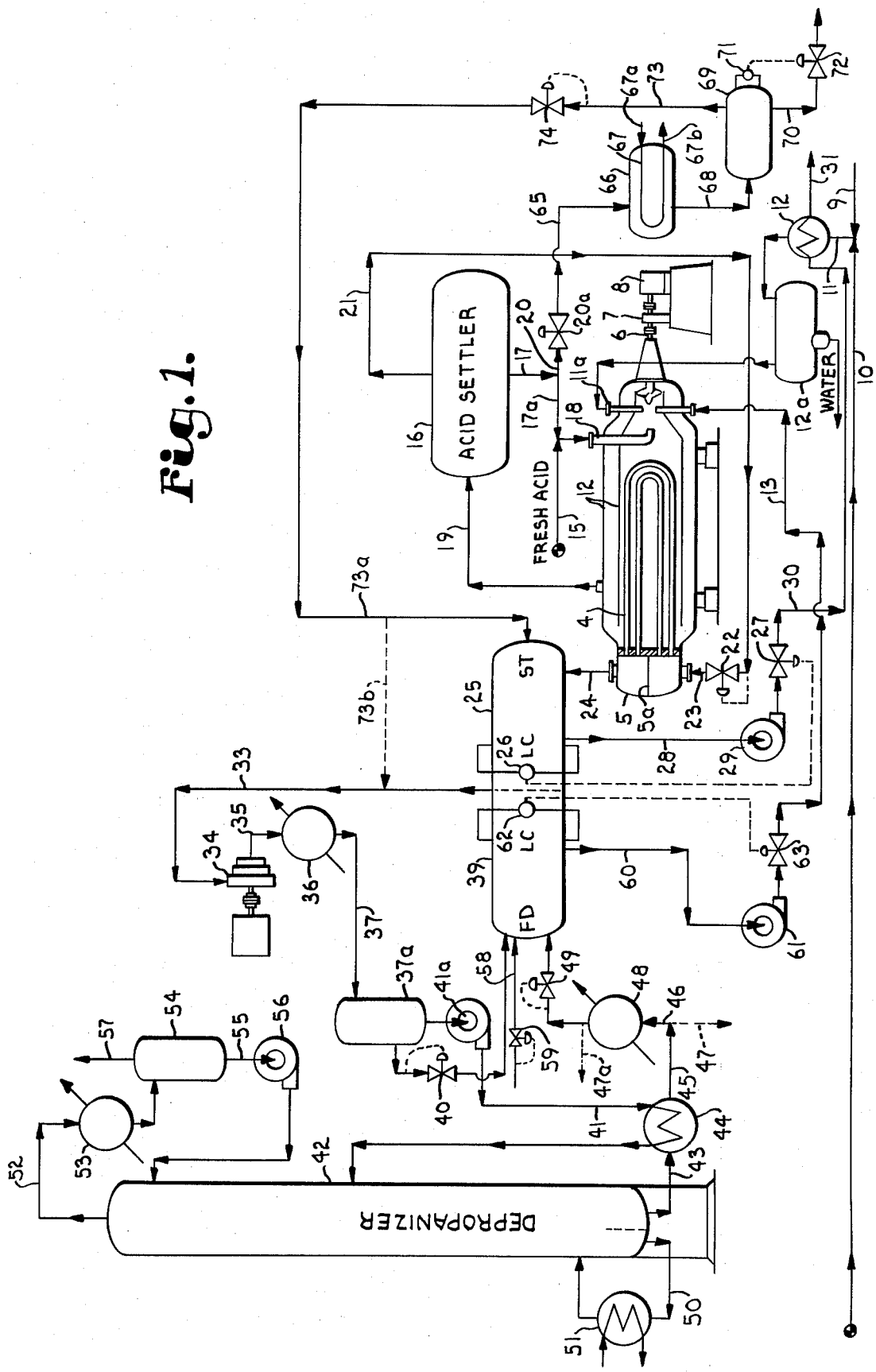

United States Patent [19]

West

[11] 3,970,720

[45] July 20, 1976

[54] RECOVERY OF HYDROCARBONS FROM ACID SETTLER BOTTOMS

[75] Inventor: Charles L. West, Shawnee Mission, Kans.

[73] Assignee: Stratford Engineering Corporation, Kansas City, Mo.

[22] Filed: May 30, 1974

[21] Appl. No.: 474,814

[52] U.S. Cl. .................... 260/683.62; 260/683.4 F
[51] Int. Cl.² ........................................ C07C 3/54
[58] Field of Search ................. 260/683.62, 683.61, 260/683.4 F, 683.59

[56] References Cited
UNITED STATES PATENTS

| | | | |
|---|---|---|---|
| 2,335,704 | 11/1943 | Smith | 260/683.62 |
| 2,649,486 | 8/1953 | Putney | 260/683.61 |
| 2,664,452 | 12/1953 | Putney | 260/683.4 F |
| 2,949,494 | 8/1960 | Putney | 260/683.62 |
| 3,192,283 | 6/1965 | Mosely et al. | 260/683.62 |
| 3,448,168 | 6/1969 | Goldsby | 260/683.62 |
| 3,652,708 | 3/1972 | Lewis et al. | 260/683.62 |

*Primary Examiner*—G. J. Crasanakis
*Attorney, Agent, or Firm*—Thomas M. Scofield

[57] ABSTRACT

Improvements in processes of alkylating isoparaffinic hydrocarbons with olefinic hydrocarbons in the presence of sulfuric acid catalyst utilizing effluent refrigeration of the alkylation reaction step; recovering hydrocarbons from spent acid removed from such alkylation systems and returning same to the system joining the heat exchanged hydrocarbon phase from the acid settler in the suction trap; using depropanizer bottoms to heat the spent acid to drive off hydrocarbons therefrom before passing same to the flash drum.

6 Claims, 1 Drawing Figure

3,970,720

RECOVERY OF HYDROCARBONS FROM ACID SETTLER BOTTOMS

BRIEF DESCRIPTION OF THE INVENTION

Processes of alkylating isoparaffinic hydrocarbons with olefinic hydrocarbons in the presence of sulfuric acid catalyst are well known to the art. U.S. Pat. No. 2,949,494 "Alkylation of Hydrocarbons Utilizing Evaporative Cooling", issued Aug. 16, 1960 to David H. Putney discloses such a process wherein effluent refrigeration is employed. The latter means that evaporative cooling of hydrocarbons is employed with indirect heat exchange to reduce the temperature of the alkylation reactants prior to and during the reaction step. The named U.S. Pat. No. 2,949,494 was an improvement over the earlier Putney U.S. Pat. No. 2,664,452 "Process for Alkylation Utilizing Evaporative Cooling" issued Dec. 29, 1953.

In both the above Putney patents, the reaction effluent, comprising a mixture of catalyst acid and hydrocarbons is discharged from the reactor to an acid settler. From the acid settler a hydrocarbon phase, including alkylate and excess isoparaffinic hydrocarbons, as well as excess normal paraffinic hydrocarbons, is discharged overhead. From the bottom of the acid settler, the acid catalyst, including some alkylate and other hydrocarbons, was recycled, as catalyst, to the reaction step. Typically, from the recycle line, spent acid was taken from the system and, additionally, fresh acid was added as makeup. The presence of alkylate and normal hydrocarbons in the spent acid has heretofore required processing. ONe alternative was to weather the spent acid prior to passing same to an acid recovery plant for burning. Another alternative was to provide an after settler, steam heated, where the hydrocarbons driven off overhead either went to a flare line (wasted) or were returned to the top of the primary settler. In the latter case, not only is there the problem of using steam in indirect heat exchange (corrosion), there is also the back pressure on the acid settler which must be overcome. Accordingly, the instant improvement shows means and methods for recovering the hydrocarbons from the spent acid utilizing a heating source inherent in the alkylation system (depropanizer bottoms) with the hydrocarbons returned to the system (at the suction trap) in such manner as to cooperate with same without fighting excessive back pressure. Yet further, the weathering or flare-off requirement is minimized or eliminated entirely, while the hydrocarbons are preserved.

OBJECTS OF THE INVENTION

A first object of the invention is to provide improvements in sulfuric acid catalyzed alkylation processes by recovering hydrocarbons from the sulfuric acid catalyst.

Another object of the invention is to provide improvements in sulfuric acid catalyzed alkylation processes utilizing effluent refrigeration by means of recovery of hydrocarbons from the sulfuric acid catalyst and returning same to the alkylation reaction system.

Still another object of the invention is to provide improvements in the character of the spent sulfuric acid discharged from a sulfuric acid catalyzed alkylation system, which improvements include removal of hydrocarbons from said spent acid, whereby same need not be weathered prior to burning in the acid recovery plantn; additionally, by removal of said hydrocarbons, taking a load from the acid plant and reducing the burning temperature required to reprocess the acid.

Another object of the invention is to provide means for and processes of removing hydrocarbons from spent acid from a sulfuric acid catalyzed alkylation process in such manner that said hydrocarbons may be returned to the system, thereby, avoiding loss thereof.

Still another object of the invention is to provide convenient, simple means for and methods of heating spent acid bottoms from the acid settler of a sulfuric acid catalyzed alklation system utilizing effluent refrigeration, said means and methods involving passing the depropanizer bottoms in indirect heat exchanging relationship with said spent acid for return to the system and prepare the acid for burning in an acid plant in optimum condition.

Other and further objects of the invention will appear in the course of the following description thereof.

The single figure is a schematic flow diagram of a sulfuric acid catalyzed alkylation system utilizing effluent refrigeration wherein the improved means for removing hydrocarbons from the spent acid are incorporated.

DESCRIPTION OF THE PROCESS

The instant improvement is most advantageously carried out with respect to a process of alkylation of isoparaffinic hydrocarbons by olefinic hydrocarbons utilizing effluent refrigeration as is seen in the U.S. Pat. No. 2,949,494, to David H. Putney, issued Aug. 16, 1960 for "Alkylation of Hydrocarbons Utilizing Evaporative Cooling". Typical reaction vessels usable in such alkylation processes are disclosed and described in Putney U.S. Pat. 2,800,307 issued July 23, 1957 for "Apparatus for Controlling Temperature Change of Blends of Fluids or Fluids and Finely Divided Solids". The basic alkylation process incorporating effluent refrigeration of the reaction step will first be described with respect to the drawing and, thereafter, the improvement of the instant invention as employed therewith.

ALKYLATION WITH EFFLUENT REFRIGERATION

Referring, then, to the drawing, at 1 is a reactor shell equipped with an open ended circulating tube 2. In one end of the circulating tube is a propeller or pump impeller 3 and in the other end of the circulating tube is a heat exchanger consisting of a tube handle 4 provided with a distributing head 5 enclosing one end of the reactor. Impeller 3 is mounted on a shaft 6 rotated through a reduction gear 7 by any suitable prime mover such as an electric motor 8.

Circulation within the reactor is established by impeller 3 through the annular space between the shell and circulating tube 2 over the tube bundles 4 and back to impeller 3. The flow may be reversed by changing the pitch of the impeller blades or reversing the direction of rotation thereof.

Olefinic hydrocarbons and isobutane are introduced to the system through lines 9 and 10, respectively, being combined in feed pipe 11 prior to passage through heat exchanger 12. After water separation at vessel 12a, the olefins and isobutane are passed into the reactor through inlet pipe 11a. Recycled isobutane returned through line 13 is introduced into the reactor through feed or inlet pipe 14 (from flash drum 39). The isoparaffinic hydrocarbons input to the reactor via line 9 include makeup isobutane and (optionally) recycle isobutane from the deisobutanizer (not shown).

Fresh acid is fed to the reactor through line 15 and recycle acid from acid settler 16 is returned through pipes 17 and 17a, the fresh and recycle acid entering the reactor through inlet pipe 18.

The hydrocarbons supplied through lines 9, 10 and 11, as well as recycle isobutane from line 13 are mixed in the reactor 1 with the acid catalyst introduced through lines 15, 17, 17a and 18. Alkylation of the isoparaffinic hydrocarbons by the olefinic hydrocarbons takes place in reactor 1, while the mixture is being rapidly circulated and agitated by impeller 3, insuring a thorough and intimate mixture of the hydrocarbons with acid catalyst. The mixture of hydrocarbons (including alkylate, excess isoparaffinic hydrocarbons and normal paraffinic hydrocarbons) and acid catalyst is discharged from reactor 1 through line 19 passing to acid settler 16 where same is permitted to separate into an acid phase and a hydrocarbon phase. The acid phase, including some non-separated hydrocarbons (alkylate, isoparaffinic hydrocarbons and normal paraffinic hydrocarbons) is recycled to line 18 in large, while a portion of the acid phase separated in settler 16 may be discarded (or treated according to the instant improvement to be described) through spent acid discharge line 20 in order to maintain a proper balance and proportioning of acid catalyst and hydrocarbon reactants in the system.

The hydrocarbon phase (including alkylate, excess isobutane or isoparaffinic hydrocarbons and normal paraffinic hydrocarbons) separated in settler 16 is discharged from the top of the settler through line 21 and back pressure on these hydrocarbons (and settler and reactor system) is reduced at back pressure valve 22, after which the liquid-vapor mixture is passed immediately through line 23 to the distributing head 5 of the reactor. Head 5 is divided by partition 5a which causes the partially vaporized hydrocarbons to pass through the tube bundle 4, thence to the opposite side of the distributing head and out through line 24.

Back pressure valve 22 is designed to hold sufficient back pressure on the reactor-settler system as to prevent vaporization of any of the hydrocarbon components contained therein. For example, when alkylating isobutane with butylenes in a system wherein a small amount of propane is also present, the reaction temperature will normally be controlled at 35°F to 55°F and the back pressure maintained on the settler by valve 22 would be of the order of 40 psig to 100 psig. Upon passing valve 22, pressure on the hydrocarbon phase of the effluent is reduced to the order of 0 psig to 10 psig causing a considerable portion of the lighter components of the effluent to vaporize and resulting in the cooling of the entire hydrocarbon effluent mixture.

Depending on the pressure established within the cooling elements or tube bundle 4 of reactor 1, the temperature of the hydrocarbon effluent phase would be reduced to a figure normally in the range of 15°F to 30°F by reduction of pressure. This chilled effluent, which is a mixture of liquid and vapor, while passing through tube bundle 4 absorbs the exothermic heat of the alkylation reaction by indirect heat exchange, resulting in vaporization of additional lighter components of the effluent.

Upon leaving the cooling elements 4 of reactor 1, the chilled and partially vaporized hydrocarbon effluent passes from the opposite side of circulating head 5 through line 24 to suction trap 25 where the vapor and liquid portions of the effluent are separated. A liquid level control 26 manipulating valve 27 regulates the discharge of the liquid phase (largely alkylate) from suction trap 25 through pipe 28. This liquid is returned by pump 29 through pipe 30 to heat exchanger 12 where it is brought into heat exchanging relationship with the incoming feed stock in line 11. From heat exchanger 12, this liquid passes through line 31 to neutralization and fractionation steps of conventional type (not shown).

Vapors separated from the effluent in suction trap 25 pass out overhead through line 33 to compressor 34 from which they are discharged through line 35 to condenser 36 where they are totally condensed, these liquids then being passed via lines 37 and 38 (after accumulation at 37a) to isobutane flash drum 39. The latter is operated at the same pressure as suction trap 25, both pressures being controlled by the suction pressure on compressor 34. Interposed in line 38 is a pressure reducing valve 40 which holds sufficient back pressure on accumulator 37a and condensor 36 to make possible total condensation of the hydrocarbons at the temperature which can be attained with the available water supply. Liquid hydrocarbons passing through valve 40 are thereby reduced in pressure causing partial vaporization and chilling of the hydrocarbons prior to their introduction into flash drum 39.

When propane is a component of any of the feed streams, a portion of the condensate in accumulator 37a is diverted through pipe 41, driven by pump 41a, to depropanizer 42. This is necessary in order to purge the system of the same amount of propane as is contained in the feed stocks, and after depropanization this stream is returned to the system through line 43 after heat exchange at 44 with the contents of line 41 from accumulator 37a. After heat exchanger 44, this stream, in line 45, may be split between line 46 returning to flash drum 39 and line 47 (or line 47a) to heat exchanger 66 in the improvement to be described or passed in its entirety either way. In the event all or part of the stream in line 45 is returned to flash drum 39, same is condensed at 48 and passed through pressure reducing valve 49. Back pressure valve 49 in line 46 functions in the same manner as reducing valve 40 previously described.

It should be understood that if minimum build-up of propane is desired n the reactor system, all of the condensate from accumulator 37a may be passed to depropanizer 42 through line 41 and returned to the system after depropanization through lines 43 and 45. In such case, none of the condensate would pass through pressure reducing valve 40. The contents of lines 43 and 45 are depropanized isobutane recycle.

Depropanizer 42 has the conventional accessories thereto including reboiling via line 50 with heat exchanger at 51 and overhead recycle through line 52 with condensation at 53, accumulation at 54 and recycle to the depropanizer 42 via line 55 through pump 56 with propane off over from accumulator 54 through line 57 out of the system.

The liquid hydrocarbons withdrawn from suction trap 25 through line 28 and passed to fractionation through line 31 are there separated into steams of propane, isobutane, normal butane, light alkylate and alkylate bottoms. Product streams of propane, normal butane, light alkylate and alkylate bottoms are normally removed from the system through lines which are not shown. The isobutane stream taken overhead from the deisobutanizer tower (not shown) may be recycled through line 58 having reduction valve 59 thereon to the flash drum 39 from which isobutane is directed back to the system via line 60 driven by pump 61. The quantity of this isobutane recycle to the system is regulated by level control 62 operating valve 63. Line 60, after valve 63 becomes line 13 to the reactor.

All of the streams entering flash drum 39 are subjected to reduced pressure established by the suction of compressor 34 and are thereby self-refrigerated. The vapors evolved in flash drum 39, as well as those from suction trap 25 are passed through common line 33 to compressor 34, while the chilled liquid from the drum, principally isobutane, is directed through line 60 to pumpp 61 and thence through valve 63 and line 13 to the reactor.

REMOVAL OF HYDROCARBONS FROM SPENT ACID

Basically stated, the instant improvement comprises passing the alkylation spent acid from the bottom of the settler to a heat exchanger to heat same above the 40° or 50° temperature of the settler bottoms. Thereafter, the heated spent acid is sent to an after settler. The overhead from the after settler passes through an adjustable back pressure valve to (preferably) the suction trap or, less preferably, the compressor suction. The bottoms from the after settler are then passed through a level control valve to storage or an acid plant.

The preferred heating medium for the heat exchanger receiving the alkylation spent acid is depropanizer bottoms (taken off either before or after condenser 48), although cooling water with or without injected steam may be employed.

The rationale and desirability of the improvement, briefy stated, is that markedly less hydrocarbon in the spent acid is desired. Under present environmental requirements, a low vapor pressure on the spent acid is required. The removal of hydrocarbons from the spent acid lowers the vapor pressure. Additionally, alkylate and butanes are recovered and do not go to a flare line (to waste).

The recovered hydrocarbons from the spent acid are preferably returned to the suction trap 25 or compressor 34 suction in line 33 rather than being returned to the top of acid settler 16. In the latter case, one would be working against the back pressure maintained in the reactor-settler system by back pressure valve 22. More hydrocarbons can be taken off from the heated spent acid in the after settler at a lower pressure.

Turning to the specific system illustrated and partially previously described, all or part of the depropanizer bottoms may be passed into line 47. This would be typically at approximately 156°F. In the event that the depropanizer bottoms are removed through line 47a after condenser 48, the temperature would be approximately 100°F.

As previously mentioned, a portion of the recycle acid catalyst (containing a small percentage of included hydrocarbons, including alkylate) is conventionally taken off through line 20 controlled by valve 20a as to quantity. In the instant system, line 65 passes to a heat exchanger 66, where the spent acid, including any hydrocarbons therewith, are raised in temperature due to the circulation of heat exchanging medium through coil 67 positioned therewithin. In the event that the heating medium is depropanizer bottoms from heater line 47 or line 47a, the depropanizer bottoms after being input to coil 67 through inlet line 67a and withdrawn therefrom through outlet line 67d are passed to flash drum 39. Water, with or without injected steam may be employed, as an alternative to use of the depropanizer bottoms. Cooling water is conventionally 85° to 90°F (gulf coast 90° to 95°F) and may be employed for this purpose. However, in the event of the use of cooling water with or without steam, a leak in the coil 67 would foul-up the spent acid recovery system. Steam also is a corrosion problem. Therefore, use of depropanizer bottoms is preferred. Use of the latter in heat exchange in coil 67 reduces the load on condenser 48.

The heated spent acid including hydrocarbons is passed via line 68 to after settler 69. Bottoms from after settler 69 are drawn off through line 70 in quantity controlled by level control 71 operating valve 72. This spent acid, with considerably reduced hydrocarbon content, is passed to storage or an acid recovery plant.

The overhead from after settler 69 is taken through line 73 to adjustable back pressure valve 74. Line 73 preferably passes to suction trap 25 as seen at 73a, but, alternatively and less preferably, may pass to the compressor 34 suction in line 33 via line 73b. The contents of line 73 comprise alkylate and butanes which are recovered and not passed to a flare line. The back pressure on after settler 69 may be maintained in the range of 5 to 15 lbs. psig via valve 74.

By removing the light ends in the gasoline boiling range from the spent acid, not only are these hydrocarbon values recovered from the system, but a load is taken off the acid plant where, if there is too much hydrocarbon present, in burning, a higher temperature than desired is present. The necessity of weathering the spent acid to remove the hydrocarbons or passing the latter to a flare line is avoided.

From the foregoing, it will be seen that this invention is one well adapted to attain all of the ends and objects hereinabove set forth together with other advantages which are obvious and which are inherent to the process.

It will be understood that certain process features, steps and sub-combinations thereof are of utility and may be employed without reference to other features, steps and process subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

I claim:

1. A process of alkylation of paraffinic hydrocarbons by olefinic hydrocarbons in the presence of sulfuric acid catalyst in a reaction step wherein:
   a. a reaction mixture of hydrocarbons and sulfluric acid catalyst is withdrawn from said reaction step,
   b. the sulfuric acid catalyst phase is separated from the hydrocarbon phase in a settling step,
   c. a major portion of said catalyst phase from said settling step is returned to said reaction step and a minor portion of said catalyst phase is treated to separate absorbed hydrocarbons prior to withdrawing said phase from the alkylation process as a spent acid stream, d. said reaction step and settling step being maintained under sufficient pressure that said reaction mixture, said hydrocarbon phase and said catalyst phase are held in liquid state, e. the pressure is reduced on the hydrocarbon phase from said settling step to vaporize volatile hydrocarbons and thus refrigerate said hydrocarbon phase and f. said refrigerated hydrocarbon phase is passed in indirected heat exchanging relationship with said reaction step to lower the temperature thereof and vaporize further volatile hydrocarbons, g. said hydrocarbon phase from said indirect heat exchanging relationship with said reaction step being passed to a first vapor-liquid separating step wherein a vapor portion of said hydrocarbon phase is separated from a liquid portion thereof and said liquid and said vapor portions being separately removed from said first separating step, the improvement which comprises:

h. heating said spent acid stream prior to withdrawing the same from said process and passing said heated stream to a second vapor-liquid separating step to separate said absorbed hydrocarbons from said spent acid, i. returning separated hydrocarbons from said second separating step to said first separating step, j. and withdrawing spent liquid acid from said second separating step.

2. A process as in claim 1 including maintaining said second vapor-liquid separating step under back pressure and releasing said back pressure on the hydrocarbon phase from said second separating step before passing same to the said first separating step.

3. In a process of alkylation of isoparafinic hydrocarbons by olefinic hydrocarbons in the presence of sulfuric acid catalyst in a reaction step, wherein:

a. a reaction mixture of hydrocarbons and sulfuric acid catalyst is withdrawn from said reaction step, b. the sulfuric acid catalyst phase is separated from the hydrocarbon phase in a settling step, and c. a major portion of the sulfuric acid catalyst phase is returned to the reaction step from the settling step and the balance of said sulfuric acid phase is withdrawn from the alkylation process as a spent acid stream, the improvement which comprises:

d. heating the said spent acid stream after withdrawal thereof from the settling step and passing said heated stream to a vapor-liquid separating step whereby to separate absorbed hydrocarbons, including alkylate, therefrom, e. passing said separating hydrocarbons from said vapor-liquid separating step to combine with the hydrocarbon phase from the settling step, and f. withdrawing the spent acid bottoms from the vapor-liquid separating step and passing same out of the alkylation process.

4. A process as in claim 3 wherein the said vapor-liquid separating step is maintained under pressure and releasing said pressure on the hydrocarbon phas from said vapor-liquid separating step before passing said hydrocarbon phase to join the hydrocarbon phase from the settling step.

5. In a process of alkylation of isoparaffinic hydrocarbons by olefinic hydrocarbons in the presence of sulfuric acid catalyst in a reaction step, wherein:

a. a reaction mixture of hydrocarbons and sulfuric acid catalyst is withdrawn from said reaction step, b. the sulfuric acid catalyst phase is separated from the hydrocarbon phase in a settling step, c. a major portion of the sulfuric acid catalyst phase is returned to the reaction step from said settling step the balance of said sulfuric acid phase is withdrawn from the alkylation process as a spent acid stream and fresh sulfuric is added to the reaction step d. the hydrocarbon phase from said settling step is passed to a first vapor-liquid separating step after indirect heat exchange of at least a portion of said hydrocarbon phase with the reaction step (a) the improvement which comprises:

e. heating the said spent acid stream after withdrawl thereof from the settling step and passing said heated stream to a second vapor-liquid separating step whereby to separate absorbed hydrocarbons, including alkylate, therefrom, f. passing said separated hydrocarbons from said second vapor-liquid separating step to combine with the hydrocarbon phase in said first vapor-liquid separating step, and g. withdrawing the spent acid bottoms from the second vapor-liquid separating step and passing same out of the alkylation process.

6. A process as in claim 5 wherein said second vapor-liquid separating step is maintained under pressure, and releasing said pressure on the hydrocarbon phase from said second vapor-liquid separating step before passing same to combine with the hydrocarbon phase from the settling step.

* * * * *